(12) United States Patent  (10) Patent No.: US 7,799,004 B2
Tumey  (45) Date of Patent: Sep. 21, 2010

(54) NEGATIVE PRESSURE WOUND TREATMENT APPARATUS AND INFECTION IDENTIFICATION SYSTEM AND METHOD

(75) Inventor: David Tumey, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 225 days.

(21) Appl. No.: 10/090,358

(22) Filed: Mar. 4, 2002

(65) Prior Publication Data

US 2002/0143286 A1  Oct. 3, 2002

Related U.S. Application Data

(60) Provisional application No. 60/273,587, filed on Mar. 5, 2001.

(51) Int. Cl.
*A61M 1/00* (2006.01)
*A61F 13/00* (2006.01)
*A61F 15/00* (2006.01)

(52) U.S. Cl. .................. 604/313; 604/318; 604/319; 602/41

(58) Field of Classification Search ......... 604/304–308, 604/313, 318, 319; 422/68.1
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |

(Continued)

FOREIGN PATENT DOCUMENTS

AU  550575 A1  8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, vol. 38, No. 6, Jun. 1997, pp. 563-577; Lippincott Williams & Wilkins, Inc., Philadelphia, PA, U.S.A.

(Continued)

*Primary Examiner*—Melanie J Hand

(57) ABSTRACT

A vacuum assisted wound closure device having a means for identifying infectious agents within a wound site. The vacuum assisted wound closure device includes a screen for placement within a wound site, a sealing means for covering the wound site, and a vacuum source in fluid communication with the screen. A canister may be disposed between the screen and vacuum source, such that fluids or other exudates that may be drawn from the wound during application of negative pressure by the vacuum source are collected in the canister for later disposal. A sensing device, which may be a gas chromatograph, sensor array, or other similar device capable of optically sensing the presence of a bacterial agent or other form of infection being drawn from the wound site, is disposed within the screen or interposed between the screen and the vacuum source.

28 Claims, 2 Drawing Sheets

U.S. PATENT DOCUMENTS

| | | | |
|---|---|---|---|
| 3,520,300 A | 7/1970 | Flower | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A * | 5/1983 | Svedman | 604/291 |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vailancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,955,391 A * | 9/1990 | Parker et al. | 600/584 |
| 4,969,880 A | 11/1990 | Zamierowski | |
| 4,985,019 A | 1/1991 | Michelson | |
| 5,037,397 A | 8/1991 | Kalt et al. | |
| 5,039,491 A * | 8/1991 | Saaski et al. | 422/82.05 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,237,523 A * | 8/1993 | Bonne et al. | 702/100 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | Debusk et al. | |
| 5,358,494 A | 10/1994 | Svedman | |
| 5,437,184 A * | 8/1995 | Shillady | 73/304 C |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,583,281 A | 12/1996 | Yu | |
| 5,607,388 A | 3/1997 | Ewall | |
| 5,611,846 A * | 3/1997 | Overton et al. | 96/102 |
| 5,636,643 A | 6/1997 | Argenta et al. | |
| 5,645,081 A | 7/1997 | Argenta et al. | |
| 5,811,255 A | 9/1998 | Hunter et al. | |
| 5,855,570 A * | 1/1999 | Scherson et al. | 604/304 |
| 6,017,440 A * | 1/2000 | Lewis et al. | 205/777.5 |
| 6,071,267 A | 6/2000 | Zamierowski | |
| 6,120,462 A * | 9/2000 | Hibner et al. | 600/566 |
| 6,135,116 A | 10/2000 | Vogel et al. | |
| 6,188,067 B1 | 2/2001 | Chutjian et al. | |
| 6,190,858 B1 * | 2/2001 | Persaud et al. | 435/4 |
| 6,192,753 B1 * | 2/2001 | Czarnek | 73/313 |
| 6,241,747 B1 | 6/2001 | Ruff | |
| 6,345,623 B1 | 2/2002 | Heaton et al. | |
| 6,398,767 B1 * | 6/2002 | Fleischmann | 604/313 |
| 6,458,109 B1 * | 10/2002 | Henley et al. | 604/304 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstream et al. | |
| 2002/0120185 A1 | 8/2002 | Johnson | |
| 2002/0143286 A1 | 10/2002 | Tumey | |

FOREIGN PATENT DOCUMENTS

| | | |
|---|---|---|
| AU | 745271 | 3/2002 |
| AU | 755496 | 12/2002 |
| CA | 2005436 | 6/1990 |
| DE | 26 40 413 A1 | 3/1978 |
| DE | 43 06 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2333965 A | 8/1999 |
| GB | 2329127 B | 8/2000 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO/94/20041 | 9/1994 |
| WO | WO 96/05873 | 2/1996 |
| WO | WO 97/18007 | 5/1997 |
| WO | WO 99/13793 | 9/1998 |

WO    WO 0059424 A1 * 10/2000

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn II, MD et al.; Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; Letter to the editor, British Journal of Plastic Surgery, 1998, vol. 51(3), p. 267: Elsevier Science/The British Assocition of Plastic Surgeons, United Kingdom.

S.E. Greer, et al.; The Use of Subatmospheric Pressure Dressing Therapy to Clos Lymphocutaneous Fistulas of the Groin; British Journal of Plastic Surgery (2000), 53, p. 484-487, Article No. BJPS2000.3360, Elsevier Science/The British Association of Plastic Surgeons, United Kingdom.

George V. Letsou, M.D., et al. .; Stimulation of Adenylate Cyclase Activity in Cultured Endothelial Cells Subjectied to Cyclic Stretch; Journal of Cardiovascular Surgery, 31, 1990, pp. 634-639; Edizonia Minerva Medica, Torino, Italy.

PCT International Search Report; PCT international application PCT/ GB98/02713; Jun. 8, 1999.

PCT Written Opinion; PCT international application PCT/GB98/ 02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/ 02802; Sep. 3, 1997.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts for the Clinical-Biological Management of the Wound Process in the Treatment of Purulent Wounds by Means of Vacuum Therapy; Vestnik Khirurgi.

International Search Report for PCT international application PCT/ GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstertics, Jul. 1987, V. 165, pp. 79-80.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, " *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

\* cited by examiner

NEGATIVE PRESSURE WOUND TREATMENT APPARATUS AND INFECTION IDENTIFICATION SYSTEM AND METHOD

RELATED APPLICATIONS

This application claims the benefit under 35 U.S.C. §119 (e), of U.S. provisional patent application No. 60/273,587 filed Mar. 5, 2001.

FIELD OF THE INVENTION

The present invention relates to vacuum assisted wound treatment systems and methods, and more particularly to vacuum assisted wound treatment systems and methods that utilize a means for identifying infection through the use of optical analysis.

BACKGROUND OF THE INVENTION

Vacuum induced healing of open wounds has recently been popularized by Kinetic Concepts, Inc. of San Antonio, Tex., by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261,893, issued Nov. 16, 1993, and U.S. Pat. No. 5,527,293, issued Jun. 18, 1996, the disclosures of which are incorporated herein by this reference. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are incorporated by reference as though fully set forth herein.

These patents, and others, addressed the problems associated with closure of many types of wounds, including large or infected wounds. Wound closure typically involves the migration of epithelial and subcutaneous tissue towards the center of the wound site. In many wounds however, this migration is slowed or non-existent due to the size of the wound, and the degree of infection. Such wounds have been commonly closed using sutures or staples, with varying results. Improved techniques, as those described in the above mentioned patents, involve applying a negative pressure to the wound over an area sufficient to promote migration of epithelial and subcutaneous tissue toward the wound. Such techniques have been met with extremely positive results, and are currently being marketed and utilized by a device known as V.A.C.® (Vacuum Assisted Closure™), manufactured by Kinetic Concepts, Incorporated, of San Antonio, Tex.

One difficulty associated with the use of the V.A.C.® device, is that no suitable means for detecting the presence or kind of infection present in the wound is available, without disturbing the airtight dressing covering the wound.

Substantial work has been performed relating to the detection of microorganisms, which include spectrometers, chromatographs, and other electronic sensors for detecting the presence of microorganisms. Exemplary U.S. patents known to applicant include Lewis, et al. U.S. Pat. No. 6,017,440 issued Jan. 25, 2000; Chutjian, et al. U.S. Pat. No. 6,188,067 issued Feb. 13, 2001; Hunter, et al. U.S. Pat. No. 5,811,255 issued Sep. 22, 1998; Overton, et al. U.S. Pat. No. 5,611,846 issued Mar. 18, 1997; and Yu U.S. Pat. No. 5,583,281 issued Dec. 10, 1996; the disclosures of which are incorporated by reference herein.

As is well known to those of ordinary skill in the art, closure of surface wounds involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but also are also less able to successfully fight bacterial infection and thus are less able to naturally close the wound. Until the advent of vacuum induced therapy, such difficult wounds were addressed only through the use of sutures or staples. Although still widely practiced and sometimes effective, such mechanical closure techniques suffer a major disadvantage in that they produce tension on the skin tissue adjacent the wound. In particular, the tensile force required in order to achieve closure using sutures or staples may cause very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return.

While V.A.C.® therapy has been highly successful in the promotion of wound closure, healing many wounds previously thought untreatable, some difficulty remains. Because the very nature of V.A.C.® therapy dictates an atmospherically sealed wound site, it is difficult to detect the presence or concentration of contaminant microorganisms, such as bacteria, that may be present in the wound site, without removing the wound dressing. It has heretofore been necessary to disturb the wound site, and thereby interrupt the therapy, in order to test for the presence or concentration of bacterial infection. Furthermore, any disturbance to the wound site may increase the possibility of infection to the wound site. Additionally, removal of the wound dressing may cause pain or discomfort to the patient.

Accordingly, a primary object of the present invention is to provide a vacuum assisted closure device that utilizes a means for detecting the presence of an infection present at a wound site during utilization of an airtight dressing, without disturbing the dressing at the wound site.

A further object of the present invention is to provide a means for identifying the nature or specific type of infection present at a wound site during the utilization of an airtight dressing, without disturbing the dressing at the wound site.

It is yet a further object of the present invention to provide a means for detecting the concentration of an infecting agent present at a wound site during utilization of an airtight dressing, without disturbing the dressing at the wound site.

SUMMARY OF THE INVENTION

In accordance with the foregoing objects, the present invention generally comprises a foam pad for insertion substantially into a wound site and a wound drape for sealing enclosure of the foam pad at the wound site. The foam pad, comprised of a foam having relatively few open cells in contact with the areas upon which cell growth is to be encouraged so as to avoid unwanted adhesions, but having sufficiently numerous open cells so that drainage and V.A.C.® therapy may continue unimpaired, is placed in fluid communication with a vacuum source for promotion of fluid drainage, as known in the art. Such communication may include a flexible tubing that is removably connected to the foam pad and the vacuum source. A connection adapter, sometimes referred to as an "elbow" adapter, an example of which is disclosed in FIG. 6 of international patent application PCT/GB96/02802 filed Nov. 14, 1996 by Heaton, et al., claiming priority to UK patent application GB2307180, filed Nov. 14, 1995, which reference is incorporated herein as though fully set forth, may be utilized to connect the flexible tubing to the wound dressing.

An infection detection means is connectable to the vacuum source, such that fluids being removed from the wound site will pass through the detection means during suction. The detection means is preferably positioned between the canister utilized to collect wound fluids in the traditional V.A.C.® and the vacuum source. However, it is to be understood that the detection means may be positioned anywhere along the line of suction from the wound site, so long as any filtration of the wound fluid occurs after passage of the fluid through the detection means.

The infection detection means is preferably comprised of an optical scanner that is capable of detecting changes in the frequency of light passing through the scanner. The frequency changes are identifiable to a particular bacterium, antigen, or other identifying source of infection. Alternative sensors include pH sensors for detecting changes in acidic concentrations of fluids being removed from the wound site during administration of negative pressure at the wound site.

Various types of detection devices may be utilized to detect the presence, concentration, and/or type of infection present in the wound site. Exemplary devices that may be utilized include those disclosed in the previously mentioned patents issued to Chutjan et al., Lewis et al., Hunter et al., and Overton et al.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims that may be drawn hereto.

Figure 1:
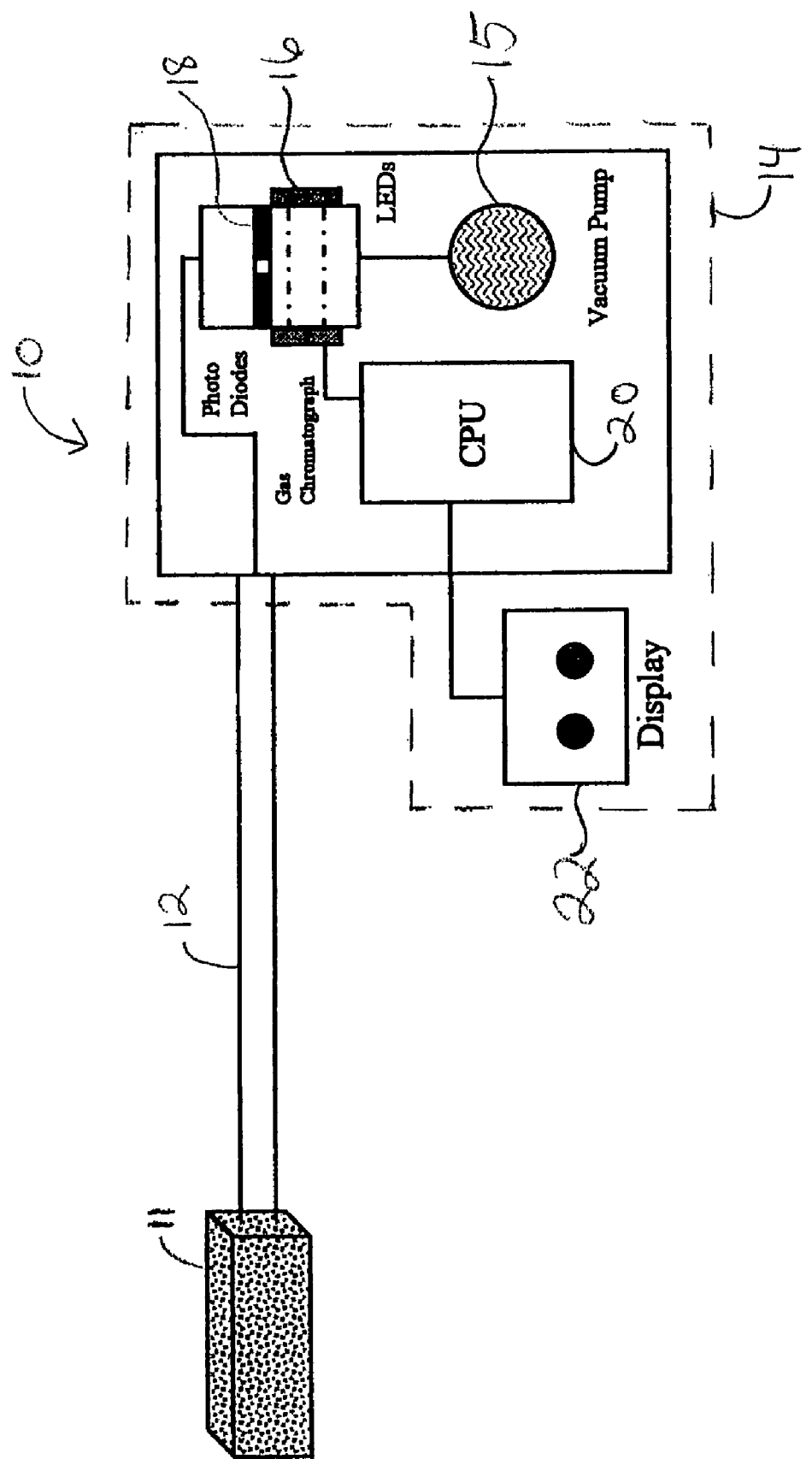
FIG. 1 shows, in schematic diagram, the preferred embodiment of the present invention as applied to a mammalian wound site.

Referring now to the figures, and to FIG. 1 in particular, the present invention 10 is shown to generally comprise a foam pad 11, or other screen means, for insertion substantially into a wound site and a sealing means, such as a wound drape (not shown), for sealing enclosure of the foam pad 11 at the wound site. Flexible tubing 12 may be utilized to fluidically connect the foam pad 11 to a vacuum source 14. The vacuum source 14, which may encompasses a vacuum pump 15 and the sensing device, which may be comprised of a gas chromatograph 16. An exemplary gas chromatograph that may be utilized is disclosed in U.S. Pat. No. 5,611,846 issued to Overton, et al. on Mar. 18, 1997, which disclosure is incorporated herein as though fully set forth. In the preferred embodiment, photo diodes 18 are utilized in conjunction with the gas chromatograph to detect changes in light frequency as the fluid being pumped from the wound site passes across the photo diodes 18. The gas chromatograph 16 identifies the changes in frequency, which may be associated with particular bacteria or antigens. Light frequencies associated with such microorganisms are stored in a database within a computer-processing unit 20. A software program compares the frequencies detected by the gas chromatograph 16 with the frequencies stored in the database. If the software identifies a match in the frequencies detected by the chromatograph 16 with that of the microorganism frequencies stored in the database, an audible and/or visual notification is transmitted through the display 22.

As will be understood by those skilled in the art, alternate sensing devices may also be utilized for detecting the presence of microorganisms in the fluid being suctioned from the wound site by the vacuum pump 15. Examples of such alternate sensing devices include, but are not limited to miniature mass spectrometers, such as that described by Chutjan, et al. in U.S. Pat. No. 6,188,067 whose disclosure is incorporated herein by reference as though fully set forth. An alternate embodiment of the present invention may utilize sensor arrays similar to those described by Lewis, et al. in U.S. Pat. No. 6,017,440, whose disclosure is incorporated herein by reference as though fully set forth. Such a sensor array utilizes sensors comprised of regions of nonconducting organic material and regions of conducting organic material compositionally different than that of the nonconducting material.

Figure 2:
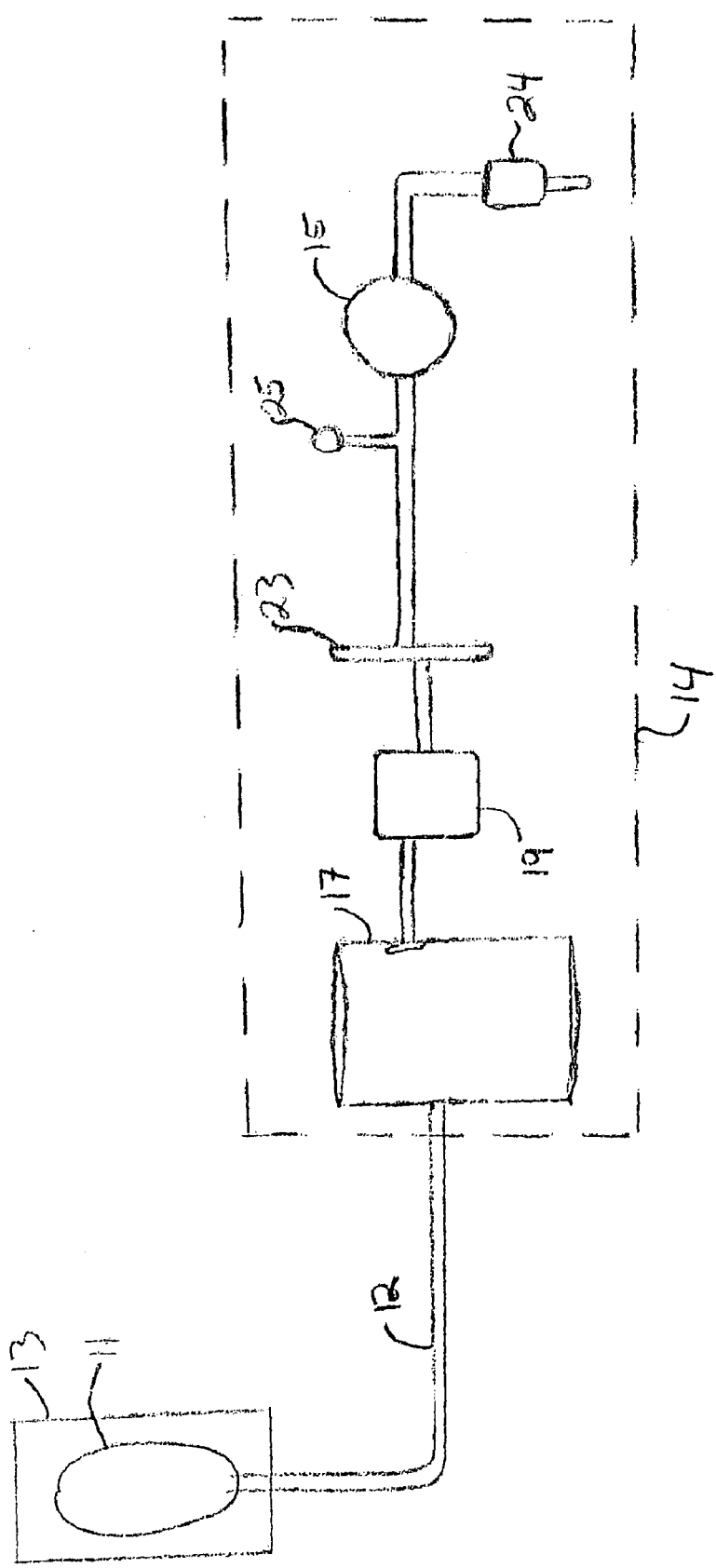
FIG. 2 is a block diagram of the preferred sensor arrangement of the present invention as applied to the wound closure device of the present invention.

The preferred sequential arrangement of the component parts of a V.A.C.® device utilizing the present invention is illustrated in FIG. 2. Such a device includes a foam pad 11 and screen means 13, such as an airtight dressing for application at the wound site. A conduit, such as flexible tubing 12, may be utilized to communicate fluids to and from the vacuum source 14, which houses a vacuum pump 15 as the source of the suction. However, it is to be understood that other means of suction may be utilized in alternative embodiments, including wall suction and other similar means. A canister 17 is connectable to the tubing 12 to capture and store fluids and other exudates extracted from the wound site during suction. The sensor 19, as described above in relation to FIG. 1, is preferably positioned between the canister 17 and the vacuum pump 15. Alternative embodiments, not shown, may allow positioning of the sensor 19 at other positions, including within the canister 17 itself, within the foam 11, dressing 13, or along the tubing 12. Additionally, automatic sampling lines may be utilized. Such positioning arrangements are dependent on the type of sensor utilized, and the limitations placed upon it due to its size and accuracy fluctuations due to direct contact with the wound fluids. The greatest accuracy lies, however, in placing the sensor 19 between the wound site and any filtration mechanisms that may be in place, which may include a hydrophobic filter or charcoal filter 23 located at the vacuum exhaust 24. A bleed orifice 25 may also be utilized to reduce the build up of excess pressure within the system.

While the foregoing description is exemplary of the preferred embodiment of the present invention, those of ordinary skill in the relevant arts will recognize the many variations, alterations, modifications, substitutions and the like are readily possible, especially in light of this description and the accompanying drawings. In any case, because the scope of the present invention is much broader than any particular embodiment, the foregoing detailed description should not be considered as a limitation of the scope of the present invention, which is limited only by the claims that may be drawn hereto.

What is claimed is:

1. A negative pressure therapy device, comprising:
   a foam pad for placement within a wound bed;
   a drape adhered over said screen means and wound bed;
   a vacuum source fluidically communicating with said foam pad;
   a gas chromatograph, operable to sense compositional characteristics of unfiltered wound fluid from the wound bed, the gas chromatograph interposed between said foam pad and said vacuum source, wherein said gas chromatograph further comprises a photo diode to detect changes in light frequency as unfiltered wound fluid from the wound bed passes the photo diode;
   a computer-processing unit comprising a database that stores light frequencies associated with microorganisms;
   a software program operable to compare the light frequency detected by the gas chromatograph with the light frequencies stored in the database; and
   a collection canister interposed between said foam pad and said gas chromatograph.

2. A negative pressure therapy device, comprising:
   a foam pad for placement within a wound bed;
   a drape adhered over said foam pad and wound bed;
   a vacuum source fluidically communicating with said foam pad;
   a flexible conduit for communicating between said foam pad and said vacuum source;
   a collection canister interposed between said foam pad and said vacuum source;
   a sensor array, operable to sense compositional characteristics of unfiltered wound fluid from the wound bed, interposed between said foam pad and said vacuum source, wherein said compositional characteristics are indicative of infection within the wound and include a presence of at least one of a bacterium or an antigen, wherein the sensor array comprises regions of nonconducting organic material, and wherein the sensor array further comprises regions of conducting organic material compositionally different than the nonconducting organic material; and
   wherein said sensor array is embedded within said foam pad.

3. The negative pressure therapy device of claim 2 further comprising a flexible conduit for communicating between said foam pad and said vacuum source.

4. The negative pressure therapy device of claim 1, wherein the microorganisms include at least one of a bacterium or an antigen.

5. The negative pressure therapy device of claim 1, further comprising:
   a display operable to transmit at least one of an audible or visual notification if the software program identifies a match, between the light frequency detected by the gas chromatograph and at least one of the light frequencies stored in the database.

6. The negative pressure therapy device of claim 1, further comprising:
   a filtration mechanism, the gas chromatograph interposed between the wound bed and the filtration mechanism.

7. The negative pressure therapy device of claim 1, wherein said gas chromatograph is embedded within said foam pad.

8. The negative pressure therapy device of claim 1, wherein said gas chromatograph is disposed on said drape, such that said gas chromatograph is in contact with said foam pad.

9. The negative pressure therapy device of claim 1, wherein said gas chromatograph is disposed within said collection canister.

10. A negative pressure therapy device, comprising:
    a foam pad for placement within a wound bed;
    a drape adhered over said foam pad and wound bed;
    a vacuum source fluidically communicating with said foam pad;
    a collection canister interposed between said foam pad and said vacuum source;
    a flexible conduit for communicating between said foam pad and said vacuum source;
    a gas chromatograph, operable to sense compositional characteristics of unfiltered wound fluid from the wound bed, the gas chromatograph interposed between said foam pad and said vacuum source, wherein said gas chromatograph further comprises a photo diode to detect changes in light frequency as unfiltered wound fluid from the wound bed passes the photo diode;
    a filtration mechanism, the gas chromatograph interposed between the wound bed and the filtration mechanism;
    a computer-processing unit comprising a database that stores light frequencies associated with microorganisms, wherein the microorganisms include at least one of a bacterium or an antigen;
    a software program operable to compare the light frequency detected by the gas chromatograph with the light frequencies stored in the database; and a display transmitting at least one of an audible or visual notification if the software program identifies a match between the light frequency detected by the gas chromatograph and at least one of the light frequencies stored in the database.

11. The negative pressure therapy device of claim 10, wherein said gas chromatograph is embedded within said foam pad.

12. The negative pressure therapy device of claim 10, wherein said gas chromatograph is disposed on said drape, such that said gas chromatograph is in contact with said foam pad.

13. The negative pressure therapy device of claim 10, wherein said gas chromatograph is disposed within said collection canister.

14. A negative pressure therapy device, comprising:
a foam pad for placement within a wound bed;
a drape adhered over said foam pad and wound bed;
a vacuum source fluidically communicating with said foam pad;
a flexible conduit for communicating between said foam pad and said vacuum source;
a collection canister interposed between said foam pad and said vacuum source;
a sensor array, operable to sense compositional characteristics of unfiltered wound fluid from the wound bed, interposed between said foam pad and said vacuum source, wherein said compositional characteristics are indicative of infection within the wound and include a presence of at least one of a bacterium or an antigen, wherein the sensor array comprises regions of nonconducting organic material, and wherein the sensor array further comprises regions of conducting organic material compositionally different than the nonconducting organic material; and
wherein said sensor array is disposed on said drape, such that said sensor array is in contact with said foam pad.

15. The negative pressure therapy device of claim 14 further comprising a flexible conduit for communicating between said foam pad and said vacuum source.

16. A negative pressure therapy device, comprising:
a foam pad for placement within a wound bed;
a drape adhered over said foam pad and wound bed;
a vacuum source fluidically communicating with said foam pad;
a flexible conduit for communicating between said foam pad and said vacuum source;
a collection canister interposed between said foam pad and said vacuum source;
a sensor array, operable to sense compositional characteristics of unfiltered wound fluid from the wound bed, interposed between said foam pad and said vacuum source, wherein said compositional characteristics are indicative of infection within the wound and include a presence of at least one of a bacterium or an antigen, wherein the sensor array comprises regions of nonconducting organic material, and wherein the sensor array further comprises regions of conducting organic material compositionally different than the nonconducting organic material; and
wherein said sensor array is disposed within said collection canister.

17. The negative pressure therapy device of claim 16 further comprising a flexible conduit for communicating between said foam pad and said vacuum source.

18. A negative pressure therapy device, comprising:
a foam pad for placement within a wound bed;
a drape adhered over said screen means and wound bed;
a vacuum source fluidically communicating with said foam pad;
a gas chromatograph, operable to sense compositional characteristics of unfiltered wound fluid from the wound bed, the gas chromatograph interposed between said foam pad and said vacuum source, wherein said gas chromatograph further comprises a photo diode to detect changes in light frequency as unfiltered wound fluid from the wound bed passes the photo diode;
a computer-processing unit comprising a database that stores light frequencies associated with microorganisms;
a software program operable to compare the light frequency detected by the gas chromatograph with the light frequencies stored in the database; and
a filtration mechanism, the gas chromatograph interposed between the wound bed and the filtration mechanism.

19. The negative pressure therapy device of claim 18, wherein the microorganisms include at least one of a bacterium, or an antigen.

20. The negative pressure therapy device of claim 18, further comprising:
a display operable to transmit at least one of an audible or visual notification if the software program identifies a match between the light frequency detected by the gas chromatograph and at least one of the light frequencies stored in the database.

21. The negative pressure therapy device of claim 18, wherein said gas chromatograph is embedded within said foam pad.

22. The negative pressure therapy device of claim 18, wherein said gas chromatograph is disposed on said drape, such that said gas chromatograph is in contact with said foam pad.

23. A negative pressure therapy device, comprising:
a foam pad for placement within a wound bed;
a drape adhered over said screen means and wound bed;
a vacuum source fluidically communicating with said foam pad;
a gas chromatograph, operable to sense compositional characteristics of unfiltered wound fluid from the wound bed, the gas chromatograph interposed between said foam pad and said vacuum source, wherein said gas chromatograph further comprises a photo diode to detect changes in light frequency as unfiltered wound fluid from the wound bed passes the photo diode;
a computer-processing unit comprising a database that stores light frequencies associated with microorganisms;
a software program operable to compare the light frequency detected by the gas chromatograph with the light frequencies stored in the database; and
wherein said gas chromatograph is embedded with said foam pad.

24. The negative pressure therapy device of claim 23, wherein the microorganisms include at least one of a bacterium or an antigen.

25. The negative pressure therapy device of claim 23, further comprising:
a display operable to transmit at least one of an audible or visual notification if the software program identifies a match between the light frequency detected by the gas chromatograph and at least one of the light frequencies stored in the database.

26. A negative pressure therapy device, comprising:
a foam pad for placement within a wound bed;

a drape adhered over said screen means and wound bed;
a vacuum source fluidically communicating with said foam pad;
a gas chromatograph, operable to sense compositional characteristics of unfiltered wound fluid from the wound bed, the gas chromatograph interposed between said foam pad and said vacuum source, wherein said gas chromatograph further comprises a photo diode to detect changes in light frequency as unfiltered wound fluid from the wound bed passes the photo diode;
a computer-processing unit comprising a database that stores light frequencies associated with microorganisms;
a software program operable to compare the light frequency detected by the gas chromatograph with the light frequencies stored in the database; and
wherein said gas chromatograph is disposed on said drape, such that said gas chromatograph is in contact with said foam pad.

27. The negative pressure therapy device of claim 26, wherein the microorganisms include at least one of a bacterium or an antigen.

28. The negative pressure therapy device of claim 26, further comprising:
a display operable to transmit at least one of an audible or visual notification if the software program identifies a match between the light frequency detected by the gas chromatograph and at least one of the light frequencies stored in the database.

\* \* \* \* \*